US008704001B2

(12) United States Patent
Masse

(10) Patent No.: US 8,704,001 B2
(45) Date of Patent: Apr. 22, 2014

(54) DEUTERATED 2-AMINO-3-HYDROXYPROPANOIC ACID DERIVATIVES

(75) Inventor: Craig E. Masse, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 152 days.

(21) Appl. No.: 13/119,318

(22) PCT Filed: Sep. 15, 2009

(86) PCT No.: PCT/US2009/057001
§ 371 (c)(1),
(2), (4) Date: Jun. 30, 2011

(87) PCT Pub. No.: WO2010/033511
PCT Pub. Date: Mar. 25, 2010

(65) Prior Publication Data
US 2011/0251131 A1    Oct. 13, 2011

Related U.S. Application Data

(60) Provisional application No. 61/192,218, filed on Sep. 16, 2008.

(51) Int. Cl.
*C07C 233/05*      (2006.01)
*A61K 31/16*       (2006.01)

(52) U.S. Cl.
USPC .......................... 564/158; 564/155; 514/616

(58) Field of Classification Search
USPC ................... 564/155, 158; 514/616
See application file for complete search history.

(56) References Cited

U.S. PATENT DOCUMENTS

| 5,654,301 | A | 8/1997 | Kohn et al. | |
| 6,221,335 | B1 * | 4/2001 | Foster | 424/1.81 |
| 6,440,710 | B1 * | 8/2002 | Keinan et al. | 435/148 |
| 6,603,008 | B1 * | 8/2003 | Ando et al. | 546/269.7 |
| 7,517,990 | B2 * | 4/2009 | Ito et al. | 546/184 |
| 2002/0041848 | A1 * | 4/2002 | Chaiken et al. | 424/9.1 |
| 2007/0082929 | A1 * | 4/2007 | Gant et al. | 514/338 |
| 2007/0197695 | A1 * | 8/2007 | Potyen et al. | 524/110 |
| 2007/0225297 | A1 * | 9/2007 | Perni et al. | 514/255.05 |
| 2008/0103122 | A1 | 5/2008 | Veltri | |

FOREIGN PATENT DOCUMENTS

| WO | WO 95/26325 A2 | 10/1995 |
| WO | WO 2007/118651 A1 | 10/2007 |

OTHER PUBLICATIONS

Baille, T. A., "The Use of Stable Isotopes in Pharmacological Research," *Pharmacological Reviews*, 33(2): 81-132 (1981).
Bialer, M. et al., "Progress Report on New Antiepileptic Drugs: A Summary of the Sixth Eilat Conference (EILAT VI)," *Epilepsy Research* 51:31-71 (2002).
Ben-Menachem, Elinor, "Lacosamide: An Investigational Drug for Adjunctive Treatment of Partial-Onset Seizures", *Drugs of Today* 44(1):35-40 (2008).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An in Vivo Study," *Journal of Neurochemistry*, 46(2): 399-404 (1986).
Fisher, M.B. et al., "The Complexities Inherent in Attempts to Decrease Drug Clearance by Blocking Sites of CYP-Mediated Metabolism," *Curr. Opin. Drug Discov. Devel.*, 9(1):101-109 (2006).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
Kushner, D.J. et al., "Pharmacological Uses and Perspectives of Heavy Water and Deuterated Compounds," *Can. J. Physiol. Pharmacol.*, 77:79-88 (1999).
Maltais, F. et al., "In Vitro and in Vivo Isotope Effects with Hepatitis C Protease Inhibitors: Enhanced Plasma Exposure of Deuterated Telaprevir versus Telaprevir in Rats," *J. Med. Chem.*, 52(24): 7993-8001 (2009).
Pieniaszek, H. J., et al., "Moricizine Bioavailability via Simultaneous, Dual, Stable Isotope Administration: Bioequivalence Implications," *J. Clin. Pharmacol*, 39: 817-825 (1999).
Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).
Wolen, R. L., "The Application of Stable Isotopes to Studies of Drug Bioavailability and Bioequivalence," *J. Clin. Pharmacol.*, 26: 419-424 (1986).
FDA Label approved Nov. 18, 2009: http://www.accessdata.fda.gov/drugsatfda_docs/label/2009/022253s004.022254s001lbl.pdf.
International Search Report Issued in PCT Application No. PCT/US2009/057001 dated: Feb. 4, 2010.
Written Opinion Issued in PCT Application No. PCT/US2009/057001, dated Feb. 4, 2010.

* cited by examiner

*Primary Examiner* — Shailendra Kumar
(74) *Attorney, Agent, or Firm* — McCarter & English, LLP; Steven G. Davis; Emily Dertz

(57) ABSTRACT

This invention relates to novel 2-amino-3-hydroxypropanoic acid derivatives and pharmaceutically acceptable salts thereof. This invention also provides compositions comprising a compound of this invention and the use of such compositions in methods of treating diseases and conditions that are beneficially treated by administering an NMDA glycine-site antagonist.

17 Claims, 1 Drawing Sheet

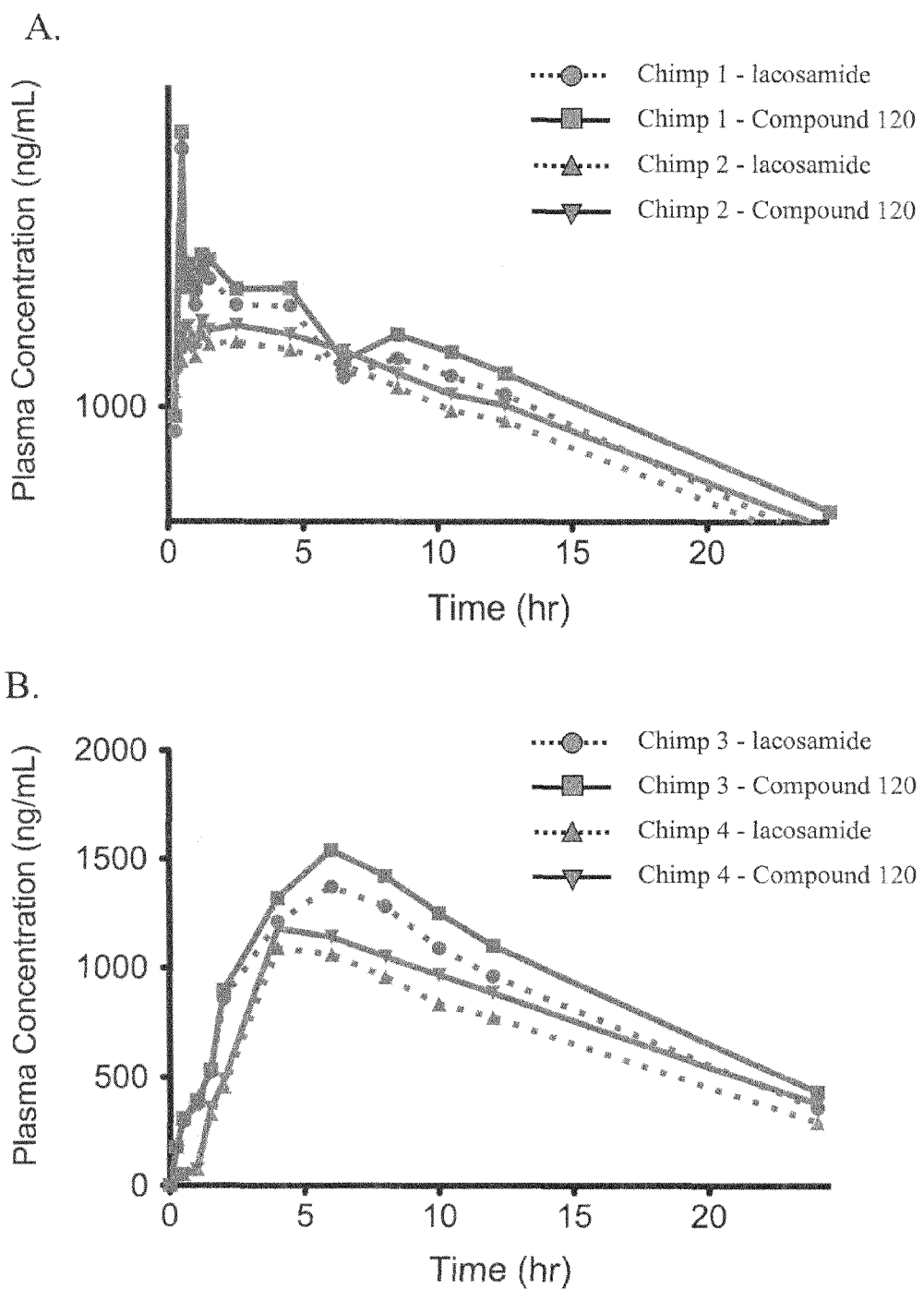

DEUTERATED 2-AMINO-3-HYDROXYPROPANOIC ACID DERIVATIVES

This application is the U.S. National Stage of PCT International Application Number PCT/US2009/057001, filed Sep. 15, 2009, which claims the benefit of U.S. Provisional Application No. 61/192,218, filed on Sep. 16, 2008.

The entire teachings of the above applications are incorporated herein by reference.

BACKGROUND OF THE INVENTION

Lacosamide, also known as 2(R)-acetamido-N-benzyl-3-methoxypropionamide, acts as an NMDA glycine-site antagonist with a dual mode of action: selectively enhancing sodium channel inactivation and modulating collapsin response mediator protein-2, (Doty, P et al, Neurotherapeutics, 2007, 4(1): 145).

Lacosamide is currently in clinical trials for epilepsy, migraine, diabetic neuropathy, fibromyalgia, and osteoarthritis.

Lacosamide is converted, in vitro, to inactive metabolites, 30% of which is the O-demethylated product. (Bialer, M et al, Epilepsy Research, 2002, 51: 31-71).

The most frequently reported adverse events among patients dosed with lacosamide include headache, dizziness, fatigue, oral paraesthesia, diplopia and nausea—generally of short duration and mild in intensity (Sachdeo, R C et al, Neurology, 2003, 60 (5, suppl. 1): Abst S54.007).

Despite the beneficial activities of lacosamide, there is a continuing need for new compounds to treat the aforementioned diseases and conditions.

SUMMARY OF THE INVENTION

This invention relates to novel 2-amino-3-hydroxypropanoic acid derivatives and pharmaceutically acceptable salts thereof. This invention also provides compositions comprising a compound of this invention and the use of such compositions in methods of treating diseases and conditions that are beneficially treated by administering an NMDA glycine-site antagonist.

BRIEF DESCRIPTION OF THE DRAWINGS

FIG. 1 depicts the time course of serum concentration of a compound of the invention and lacosamide after intravenous (panel A) or oral co-administration (panel B) of both in chimps.

DETAILED DESCRIPTION OF THE INVENTION

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of lacosamide will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al, Seikagaku 1994, 66:15; Gannes L Z et al, Comp Biochem Physiol Mol Integr Physiol 1998, 119:725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3340 (50.1% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that differs from a specific compound of this invention only in the isotopic composition thereof.

The term "compound," when referring to the compounds of the invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as net forth above the relative amount of such isotopologues will be less than 49.9% of the compound.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly, or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "$^t$", and "t-" each refer to tertiary. "US" refers to the United States of America. Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula

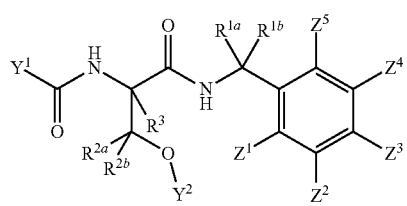

I or a pharmaceutically acceptable salt thereof, wherein:
$Y^1$ is selected from $CH_3$, $CH_2D$, $CHD_2$ or $CD_3$;
$Y^2$ is selected from $CH_3$, $CH_2D$, $CHD_2$ or $CD_3$;
each Z variable is independently selected from hydrogen or deuterium; and
each R variable is independently selected from hydrogen or deuterium;
provided that when $Y^1$ and $Y^2$ are each $CH_3$ and each Z variable is hydrogen, then at least one R variable is deuterium.

One embodiment of this invention provides compounds of Formula I where $Y^1$ is $CH_3$ or $CD_3$ and $Y^2$ is $CH_3$ or $CD_3$. Various aspects of the embodiment where $Y^1$ is $CH_3$ or $CD_3$ and $Y^2$ is $CH_3$ or $CD_3$ include those compounds where:
(a) each R variable is hydrogen;
(b) each Z variable is hydrogen;
(c) each R variable is hydrogen and each Z variable is hydrogen;
(d) each R variable is hydrogen and each Z variable is deuterium;
(e) each $R^1$ variable is deuterium, each $R^2$ and $R^3$ variable is hydrogen, and each Z variable is hydrogen;
(f) each $R^1$ and $R^2$ variable is deuterium, each $R^3$ variable is hydrogen, and each Z variable is hydrogen;
(g) each R variable is deuterium and each Z variable is hydrogen; and
(h) each $R^1$ variable is deuterium, each $R^2$ and $R^3$ variable is hydrogen, and each Z variable is deuterium;
(i) each $R^1$ and $R^2$ variable is deuterium, each $R^3$ variable is hydrogen, and each Z variable is deuterium; and/or
(j) each R variable is deuterium and each Z variable is deuterium.

Another embodiment of this invention provides compounds of Formula I where $Y^1$ is $CH_3$ and $Y^2$ is $CD_3$. Various aspects of the embodiment where $Y^1$ is $CH_3$ and $Y^2$ is $CD_3$ include those compounds where:
(a) each R variable is hydrogen and each Z variable is hydrogen;
(b) each R variable is hydrogen and each Z variable is deuterium;

(c) each $R^1$ variable is deuterium, each $R^2$ and $R^3$ variable is hydrogen, and each Z variable is hydrogen;
(d) each $R^1$ and $R^2$ variable is deuterium, each $R^3$ variable is hydrogen, and each Z variable is hydrogen;
(e) each R variable is deuterium and each Z variable is hydrogen; and/or
(f) each $R^1$ variable is deuterium, each $R^2$ and $R^3$ variable is hydrogen, and each Z variable is deuterium.

Another embodiment of this invention provides compounds of Formula I where $Y^1$ is $CD_3$ and $Y^2$ is $CD_3$. Various aspects of the embodiment where $Y^1$ is $CD_3$ and $Y^2$ is $CD_3$ include those compounds where:
(a) each Z is hydrogen;
(b) each Z is deuterium;
(c) each Z is hydrogen and each $R^1$ is deuterium,
(d) each Z is hydrogen and each $R^1$ and $R^2$ variable is deuterium; and/or
(e) each Z is deuterium and each $R^1$ is deuterium.

Another embodiment of this invention provides compounds of Formula I where each $R^1$ is deuterium. Various aspects of the embodiment where:
(a) $Y^2$ is $CD_3$;
(b) each Z is hydrogen or each Z is deuterium;
(c) $Y^2$ is $CD_3$ and each Z is hydrogen or each Z is deuterium;
(d) $Y^2$ is $CD_3$ and each Z is deuterium;
(e) $Y^2$ is $CD_3$ and each Z is hydrogen; and/or
(f) $Y^1$ and $Y^2$ are each $CD_3$.

Examples of specific compounds of Formula I include compounds 100-126 shown below:

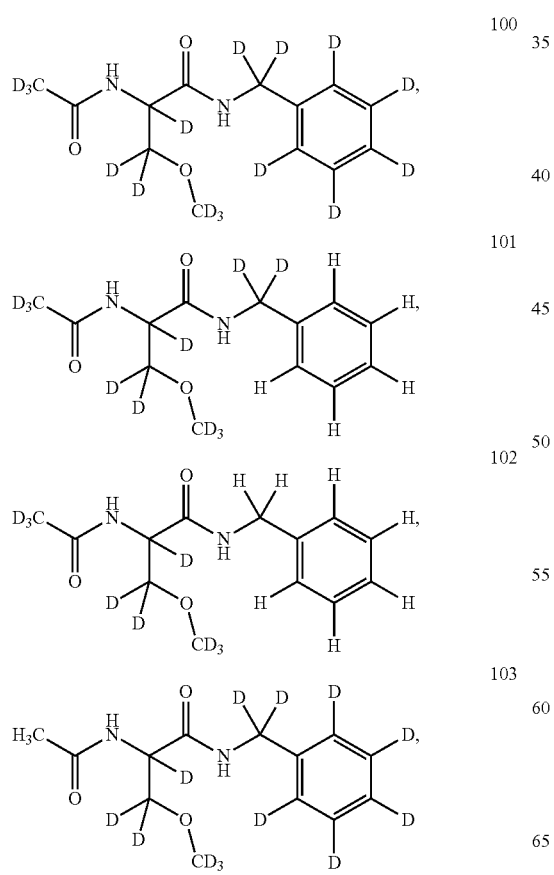

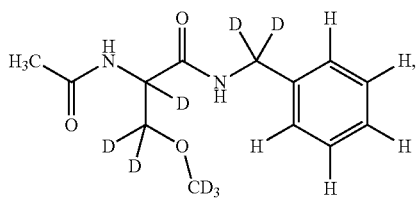

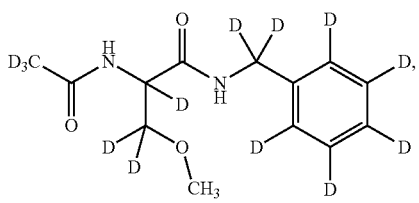

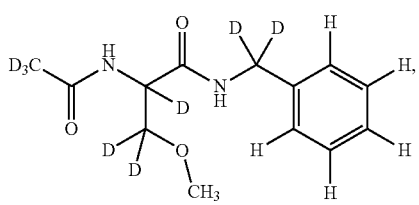

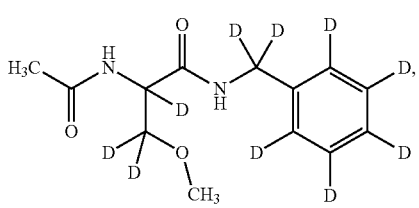

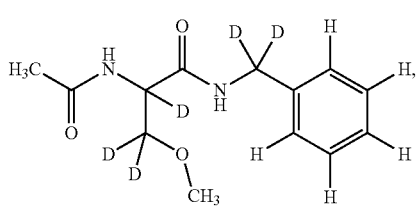

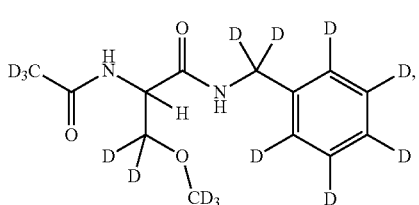

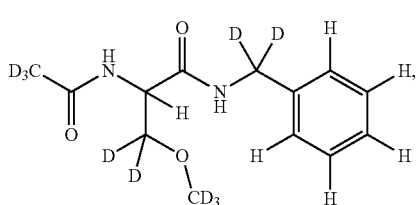

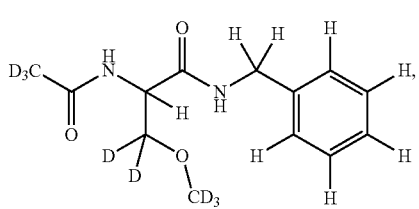

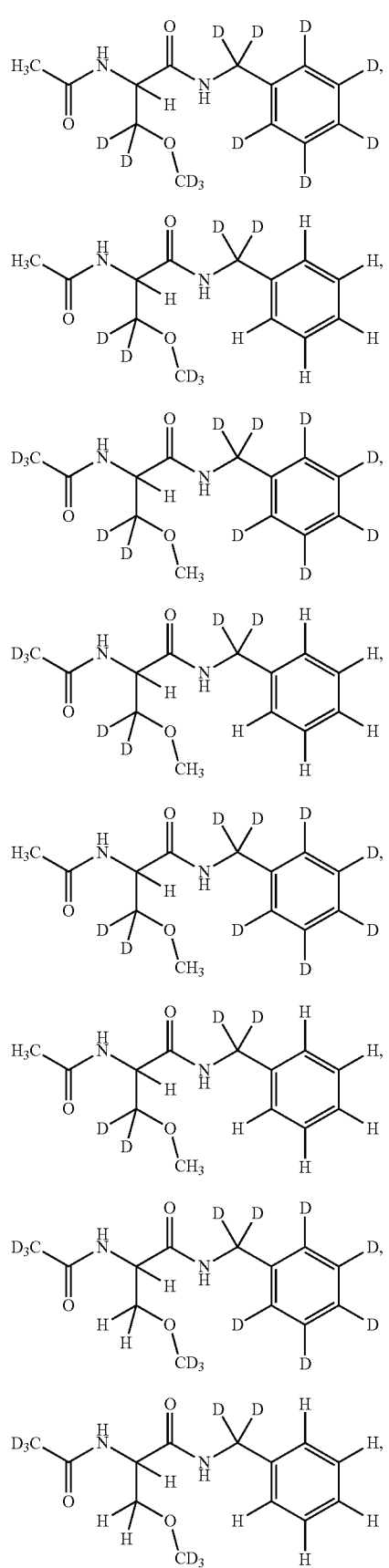
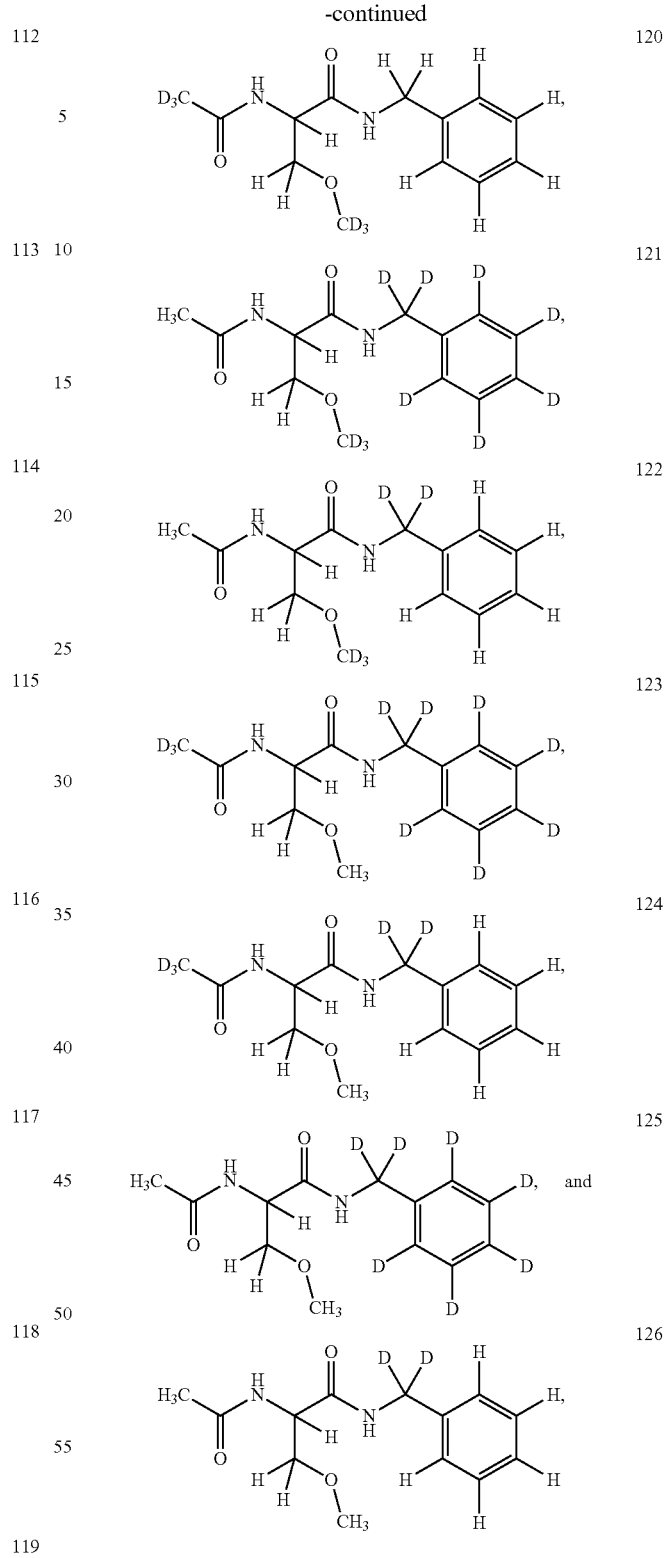

or a pharmaceutically acceptable salt of any of the foregoing.

Another example of a specific compound of Formula I is an (R) enantiomers of any one of Compounds 100-126, which is substantially free of the corresponding (S) enantiomer.

Still another example of a specific compound of Formula I is an (S) enantiomers of any one of Compounds 100-126, which is substantially free of the corresponding (R) enantiomer.

A further example of a specific compound of Formula I is compound 127R:

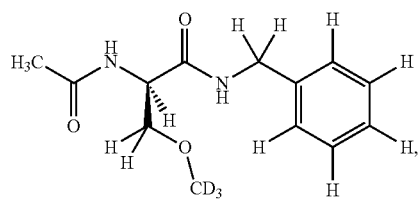

or a pharmaceutically acceptable salt thereof

In another set of embodiments, any atom not designated as deuterium in any of the embodiments or compounds set forth above is present at its natural isotopic abundance.

Exemplary Synthesis

Compounds of Formula I may be prepared in a manner analogous to the known methods for preparing non-deuterated lacosamide. A preferred synthetic route described by Kohn, H et al, Tetrahedron Asymm 1998, 9:3841 is shown in Scheme 1 below.

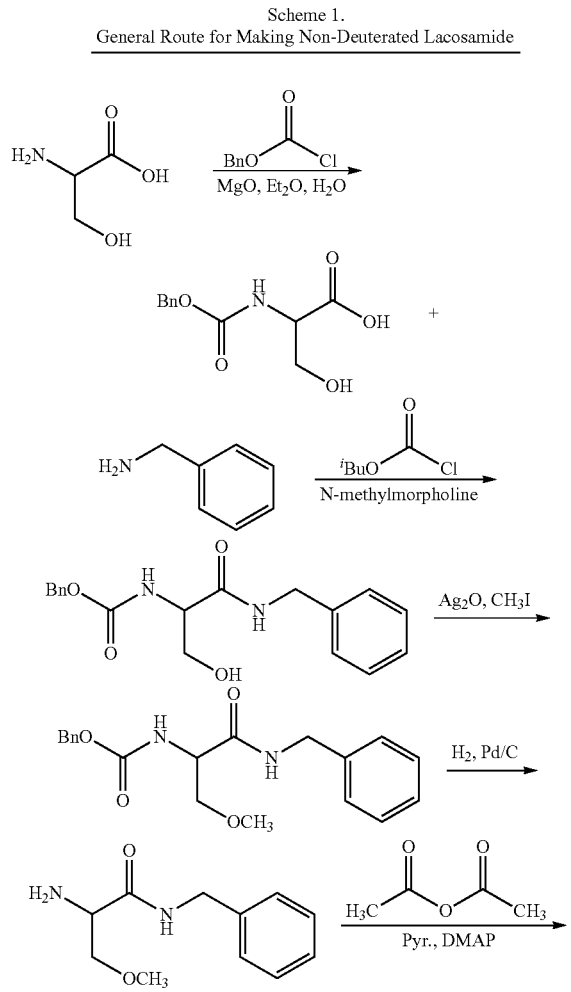

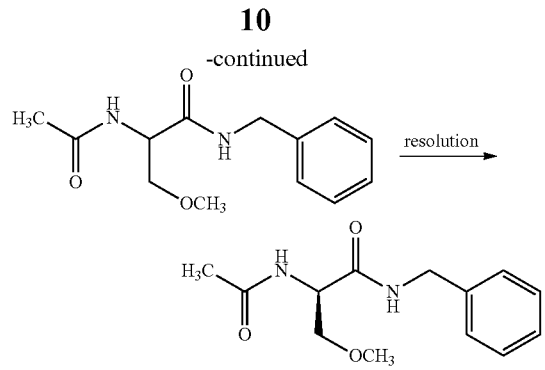

Compounds of Formula I may be prepared from racemic serine and appropriately deuterated starting materials in a manner analogous to that depicted in Scheme 1 above, Conversely, compounds of Formula I may be prepared from (R) or (S)-serine and appropriately deuterated starting materials in a manner analogous to that depicted in Scheme 1 above.

It would be apparent to one skilled in the art that various starting materials and/or intermediates in Scheme 1 may be replaced by the appropriate deuterated analogues to obtain the desired deuterated versions of lacosamide. For example, the following deuterated reagents and building blocks are commercially available:

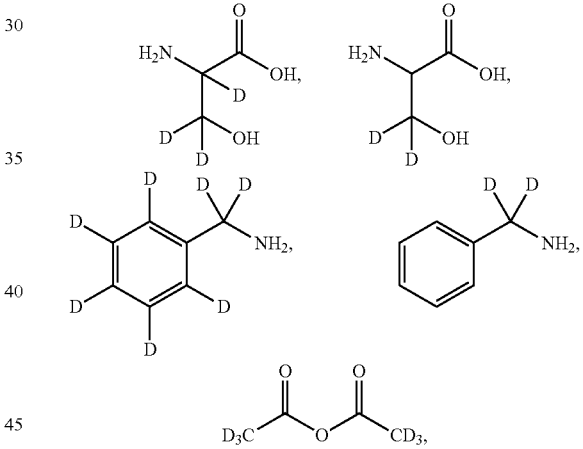

and iodomethane-$d_3$. Other deuterated building blocks that can be used to obtain the desired deuterated versions of lacosamide are known or available by known methods for making deuterated compounds of a similar nature.

Compounds of Formula I can be prepared in a manner analogous to that shown in Scheme 1 above using appropriately deuterated reagents such as those shown above. For example, appropriately deuterated serine (2-amino-3-hydroxypropanoic acid), after CBz (carboxybenzoyl) protection of the amine moiety, can be coupled with the appropriately deuterated benzyl amine to form the deuterated benzamide. Subsequent alkylation of the hydroxyl functionality with methyl iodide can be followed by deprotection of the CBz protected amine under palladium catalyzed hydrogenation conditions to afford the deuterated N-benzyl-2-amino-3-methoxypropionamide. Treatment of the resultant free amine with acetic anhydride affords the deuterated N-benzyl-2-acetamido-3-methoxypropionamide as the racemic mixture. The final resolution step may be carried out as described for non-deuterated lacosamide by chiral chromatography (see PCT Publication No. WO 00/00463) or by recrystallization (see J Med Chem 1996, 39: 1907). For other useful references see WO 97/33861; U.S. Pat. No. 5,773,475; U.S. Pat. No. 6,048,899; and EP 1642889. The specific approaches and compounds shown above are not intended to be limiting.

Compositions

The invention also provides pyrogen-free compositions comprising a compound of Formula I (e.g., including any of the formulae herein), or a pharmaceutically acceptable salt of said compound; and an acceptable carrier. In one embodiment, the composition comprises an effective amount of the compound or pharmaceutically acceptable salt thereof. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, 21st Edition, Lippincott Williams & Williams, Philadelphia, Pa. (2005).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or anon-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain along-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as lacosamide. Such agents include those indicated as being useful in combination with lacosamide, including but not limited to, those described in WO 2006079547.

Preferably, the second therapeutic agent is an agent useful in the treatment or prevention of a disease or condition selected from epilepsy and other CNS disorders; stroke and other ischemic disorders; neuropathic pain, notably diabetic distal sensory polyneuropathy, mononeuropathy or atypical facial neuropathic pain, or trigeminal neuralgia; non-neuropathic pain including chronic inflammatory pain, rheumatoid arthritis pain and/or secondary inflammatory osteoarthritis pain; tumor pain, in particular bone cancer pain, chemotherapy-induced pain and nucleoside-induced pain; non-inflammatory muscle pain, in particular fibromyalgia, myofacial pain syndrome or back pain; chronic headache, particularly migraines; primary and/or secondary dyskinesias such as Huntington's chorea, cerebral palsy, tardive or L-DOPA-induced dyskinesias; amyotrophic lateral sclerosis (ALS) and other motoneuron diseases and peripheral neuropathies; spinal muscular atrophy; progressive bulbar palsy; Guillain-Barré syndrome; Charcot-Marie-Tooth syndrome; tremor and related disorders, including primary orthostatic tremor, undetermined tremor syndrome, dystonic tremor, task- and position-specific tremors, Holmes tremor, neuropathic tremor syndrome and myorrhythmia; bipolar disease; allodynia; and schizophrenia.

In another embodiment, the invention provides separate dosage forms of a compound of this invention or pharmaceutically acceptable salt thereof and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In one embodiment of the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al, (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 1 to about 8000 mg per treatment. In more specific embodiments the range is from about 10 to 4000 mg, or from about 20 to 1600 mg, or most specifically from 100 to 800 mg. Treatment typically is administered one to two times daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for lacosamide.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of an NMDA glycine-site (e.g., antagonizing) in a cell, comprising contacting the cell with one or more compounds of Formula I herein.

According to another embodiment, the invention provides a method of treating a disease that is beneficially treated by lacosamide comprising the step of administering to a patient in need thereof an effective amount of a compound or pharmaceutically acceptable salt thereof or a composition of this invention. Such diseases are well known in the art and are disclosed in, but not limited to the following patents and published applications: WO 1997033861, U.S. Pat. No. 5,773,475, WO 1999003460, WO 2000000463, WO 2002015922, WO 2002074784, WO 2002074297, WO 2005053667, WO 2005092313, WO 2005099740, WO 2005110390, WO 2005120539, WO 2005120476, WO 2006000397, WO 2006021412, WO 2006037574, WO 2006079547, US 2007043120. Such diseases include, but are not limited to, epilepsy and other CNS disorders; stroke and other ischemic disorders; neuropathic pain, notably diabetic distal sensory polyneuropathy, mononeuropathy or atypical facial neuropathic pain, or trigeminal neuralgia; non-neuropathic pain including chronic inflammatory pain, rheumatoid arthritis pain and/or secondary inflammatory osteoarthritis pain; tumor pain, in particular bone cancer pain, chemotherapy-induced pain and nucleoside-induced pain; non-inflammatory muscle pain, in particular fibromyalgia, myofacial pain syndrome or back pain; chronic headache, particularly migraines; primary and/or secondary dyskinesias such as Huntington's chorea, cerebral palsy, tardive or L-DOPA-induced dyskinesias; amyotrophic lateral sclerosis (ALS) and other motoneuron diseases and peripheral neuropathies; spinal muscular atrophy; progressive bulbar palsy; Guillain-Barré syndrome; Charcot-Marie-Tooth syndrome; tremor and related disorders, including primary orthostatic tremor, undetermined tremor syndrome, dystonic tremor, task- and position-specific tremors, Holmes tremor, neuropathic tremor syndrome and myorrhythmia; bipolar disease; allodynia; and schizophrenia.

In one particular embodiment, the method of this invention is used to treat a disease or condition selected from epilepsy, migraine, diabetic neuropathic pain, fibromyalgia, and osteoarthritis in a patient in need thereof.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with lacosamide. The choice of second therapeutic agent is also dependent upon the particular disease or condition to be treated.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I, or a composition comprising a compound of Formula I, for use in the treatment or prevention in a patient of a disease, disorder or symptom thereof delineated herein.

Pharmaceutical Kits

The present invention also provides kits for use to treat epilepsy, migraine, diabetic neuropathy, fibromyalgia, and osteoarthritis. These kits comprise (a) a pharmaceutical composition comprising a compound of Formula I or a salt thereof, wherein said pharmaceutical composition is in a container; and (b) instructions describing a method of using the pharmaceutical composition to treat epilepsy, migraine, diabetic neuropathy, fibromyalgia, and osteoarthritis.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-scalable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of (R)-2-Acetamido, N-benzyl-3-(methoxy-d₃)propanamide (127R)

Scheme 2: Preparation of Compound 127 R.

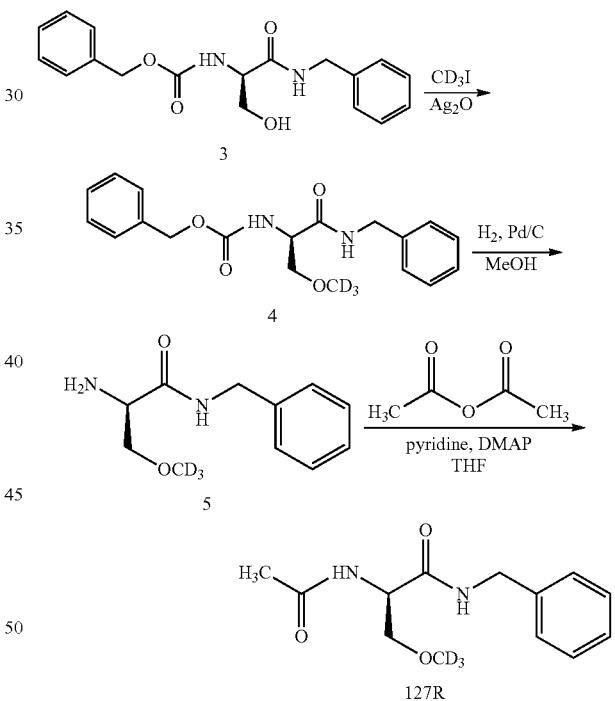

Step 1. Synthesis of (R)-Benzyl (1-(Benzylamino)-3-(methoxy-d)-1-oxopropan-2-ylcarbamate (4)

Intermediate 3 (1.50 g; 0.0046 moles, prepared from D-serine as described in Kohn, H et al, Tetrahedron Asymmetry, 1998, 9: 3841) was placed in a round bottom flask which was maintained under an atmosphere of nitrogen. The solid was then dissolved in 50 ml of CD₃I. To the solution was then added Ag₂O (5.29 g; 0.0228 moles; 5.00 eq.). The round bottom flask was then wrapped in aluminum foil and the flask was then heated to 35° C., overnight under an atmosphere of nitrogen. The reaction mixture was then filtered through Celite and the organic filtrate was concentrated in vacuo. The crude product was purified by silica gel chromatography using a gradient from 100% $CHCl_3$ to 95% $CHCl_3$/5% methanol. Column fractions containing the desired product were combined and concentrated in vacuo.

A total of 1.54 g (96% yield) of purified 4 was obtained.

Step 2. Synthesis of (R)-2-Amino-N-benzyl-3-(methoxy-$d_3$)propanamide (5)

A solution of 4 (1.54 g; 0.0079 moles) in 50 mL of methanol was purged with nitrogen gas and to the flask was then added Pd/C (0.042 g; 0.0003944 moles; 0.05 eq.). The nitrogen gas was then removed from the flask and hydrogen gas was introduced from a balloon cannula. The reaction was stirred for 3 hours at ambient temperature. The resulting mixture was filtered through Celite and the organic filtrate was concentrated in vacuo. A total of 1.03 g (62% yield) of product 5 was obtained.

Step 3, Synthesis of (R)-2-Acetamido, N-benzyl-3-(methoxy-$d_3$)propanamide (127R)

To a solution of 5 (1.03 g; 0.0049 moles) in 10 ml of THF were successively added in the following order: pyridine (0.39 ml; 0.386 g; 1.0 eq.); 4-dimethylaminopyridine (DMAP) (0.596 g; 0.0049 moles; 1.0 eq.); and finally acetic anhydride (0.46 ml; 0.498 g; 0.0049 moles; 1.0 eq.). The reaction was stirred for 1 hour at ambient temperature. The solution was then concentrated in vacuo to afford a solid. The crude solid was purified by silica gel chromatography using a gradient from 100% $CHCl_3$ to 90% $CHCl_3$/10% methanol. Column fractions containing the desired product were combined and concentrated in vacuo to afford 0.753 g (61% yield) of product 6 as an off-white powder. $^1$H-NMR (CDCl$_3$): δ 2.00 (s, 3H, —NHCOOCH$_3$); 3.43 (d of t, 1H, —CH—C H$_a$H$_b$—OCD$_3$; J=1.0 Hz; J=9 Hz); 3.80 (q of d, 1H, —CH—CH$_a$H$_b$—OCD$_3$ J=1.0 Hz; J=9 Hz); 4.47 (d, 2H CO—NH—CH$_2$—C$_6$H$_5$ J=15 Hz); 4.54 (m, 1H, α-CH-methine); 6.45 (br.d. 1H, CO—NH-amide; J=3.0 Hz); 6.78 (br.s. 1H, CO—NH-amide); 7.25-7.36 (m, 5H, ArH). MS (M+H): 254.

Example 2

Synthesis of (R)-2-(Acetamido-$d_3$)-N-benzyl-3-(methoxy-$d_3$)propanamide (120R)

Scheme 3: Preparation of Compound 120:

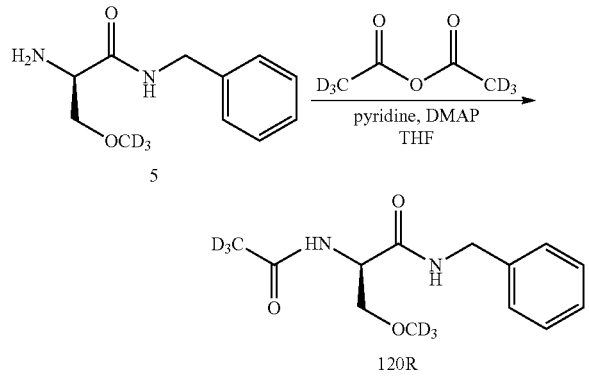

Synthesis of (R)-2-(Acetamido-$d_3$)-N-benzyl-3-(methoxy-$d_3$)propanamide (120)

To a stirred solution of 5 (2.05 g; 0.0097 moles) in 50 ml of THF were added sequentially the following reagents: pyridine (0.785 ml; 0.767 g; 0.0097 moles; 1.0 eq.); 4-dimethylaminopyridine (DMAP) (1.195 g; 0.0097 moles; 1.0 eq) and finally acetic anhydride-$d_6$ (0.912 ml; 1.049 g; 0.0097 moles; 1.0 eq.). The reaction was stirred for 1 hour at ambient temperature. The solution was then concentrated in vacuo and the crude product was purified by silica gel chromatography using 90% $CHCl_3$/10% methanol/1% aqueous $NH_4OH$. Column fractions which contained the desired product were combined and concentrated in vacuo. A total of 0.759 g (30% yield) of Compound 120 was obtained as a light yellow solid. $^1$H-NMR (CDCl$_3$): δ 3.45 (d of d; 1H—CH—C H$_a$H$_b$—OCD$_3$; J=9.1 Hz; J=9.4 Hz); 3.81 (d of d; 1H; —CH—CH$_a$H$_b$—OCD$_3$; J=4.3 Hz; J=9.4 Hz); 4.48 (overlapping d; 2H; —CO—NH—CH$_2$—C$_6$H$_5$ J=2.7 Hz); 4.57 (m; 1H; α-CH-methine); 6.50 (d; 1H; —CO—NH-amide; 3.0 Hz); 6.80 (br.s.; 1H; —CO—NH-amide); 7.26-7.37 δ (m, 5H, ArH). MS (M+H): 257.

Example 3

Pharmacokinetic Study of Lacosamide and Compound 120 in Chimps After Oral and Intravenous Dosing Lacosamide and Compound 120 (250 mgs each) were separately dissolved in water at a concentration at 2 mg/mL. A 1:1 mixture of the two compounds was then prepared containing a final concentration of 1 mg/mL of each compound and the mixture was then sterile filtered through a 0.2-μm filter.

Two chimps (one male and one female) were used in each of the oral and intravenous studies. Animals were fasted overnight prior to administration of compounds. All animals were sedated with ketamine (approximately 10 mg/kg) and/or telazol (approximately 5 mg/kg) prior to dosing. Intravenous administration was achieved by IV infusion of 50 mg of each compound (50 mL total dosing solution) over 30 minutes. Oral administration was achieved by oral gavage of a single 50 mg dose of each compound (50 mL total dosing solution). Blood samples (4.5 mL) were collected from the dosed chimps at various times prior to and after dosing. For intravenous administrations blood samples were collected at 0 min (preinfusion), 15 min, 29.5 min (immediately before the end of the infusion), then 6, 15, 30 and 45 min, and 1, 2, 4, 6, 8, 10, 12 and 24 hr after the infusion is stopped. For oral administrations, blood samples were collected at 0 min (predose), 15 and 30 min, and 1, 1.5, 2, 4, 6, 8, 10 and 12 hr postdose.

Blood samples were placed in tubes containing sodium heparin, mixed and stored on ice until centrifuged. Within 30 minutes of collection, plasma was isolated by centrifuging the blood samples and dividing the resulting plasma (approx. 2 ml) between two 96-deepwell plates. Each plate was sealed and stored at −70° C. until further analysis by LC-MS/MS using an Applied Bio-systems API 4000 mass spectrometer.

Urine was collected for 24 hours post-dose for each test animal and stored on ice. Total volume was measured and an aliquot was stored at −70° C. until further analysis Samples were analyzed by LC-MS/MS using an Applied Bio-systems API 4000 mass spectrometer. FIG. 1 shows data for each chimp administered lacosamide and Compound 120 intravenously (panel A) or orally (panel B). Table 1 below shows the AUC and $C_{max}$ values observed in each chimp. Table 2 shows the average amount of unmetabolized compound found in the urine of chimps co-administered both compounds either orally or intravenously.

TABLE 1

AUC and $C_{max}$ Values Following Co-administration of Compound 120 and Lacosamide to Chimps.

| Plasma | Chimp 1 IV | Chimp 2 | Chimp 3 | Chimp 4 PO |
|---|---|---|---|---|
| $AUC_{(0-24)}$ Compound 120 (hr * ng/mL) | 31330 | 25373 | 23090 | 17983 |
| $AUC_{(0-24)}$ Lacosamide (hr * ng/mL) | 27567 | 23037 | 20441 | 15860 |
| $C_{max}$ Compound 120 (ng/mL) | 5280 | 1690 | 1540 | 1180 |
| $C_{max}$ Lacosamide (ng/mL) | 4770 | 1560 | 1370 | 1090 |

As can be seem from Table 1 and FIG. 1, Compound 120 demonstrated a higher AUG and $C_{max}$ than lacosamide following either intravenous or oral administration to chimps.

TABLE 2

Unmetabolized Compound Found in Urine Following Co-administration of Compound 120 and Laeosamide to Chimps.

| | Urine (ng/ML) | |
|---|---|---|
| | IV | PO |
| Lacosamide | 9515 | 2720 |
| Compound 120 | 11025 | 3195 |

Table 2 demonstrates that a greater amount of Compound 120 than lacosamide was excreted in the urine intact following either intravenous or oral administration to chimps.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:

1. A compound of formula I:

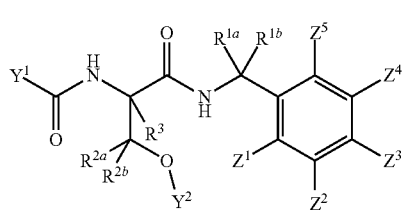

or a pharmaceutically acceptable salt thereof, wherein:
$Y^1$ is $CD_3$;
$Y^2$ is $CD_3$;
each Z variable is independently selected from hydrogen and deuterium; and
each R variable is independently selected from hydrogen and deuterium.

2. The compound of claim 1 wherein each Z variable is hydrogen.

3. The compound of claim 1 wherein each Z is deuterium.

4. The compound of claim 1 which is selected from the group consisting of the following:

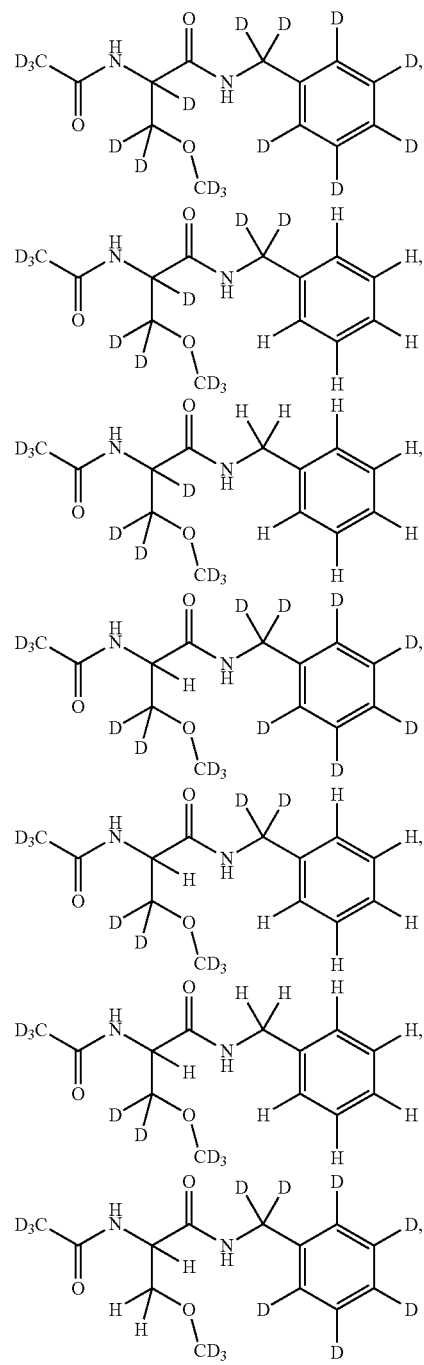

-continued

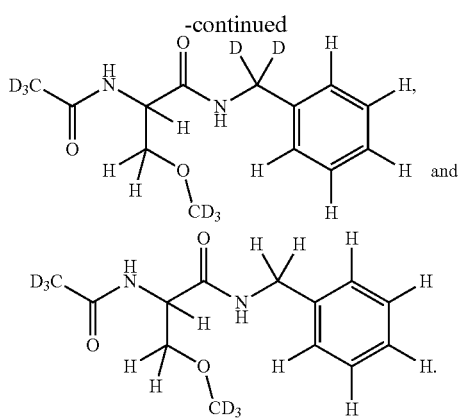

or a pharmaceutically acceptable salt of any of the foregoing.

5. The compound of claim 4, wherein the compound is an (R) enantiomer, or a pharmaceutically acceptable salt thereof, which is substantially free of the corresponding (S) enantiomer.

6. The compound of claim 4, wherein the compound is an (S) enantiomer, or a pharmaceutically acceptable salt thereof, which is substantially free of the corresponding (R) enantiomer.

7. A compound of the following formula:

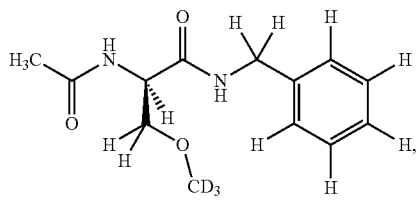

or a pharmaceutically acceptable salt thereof.

8. The compound of claim 1, wherein any atom not designated as deuterium is present at its natural isotopic abundance.

9. A composition comprising a compound of claim 1 and a pharmaceutically acceptable carrier.

10. The composition of claim 9 for use in treating a disease or disorder associated with aberrant NMDA receptor function.

11. The composition of claim 9 for use in treating epilepsy, diabetic neuropathic pain, fibromyalgia, osteoarthritis, or migraine.

12. The compound of claim 4, wherein the compound has the formula:

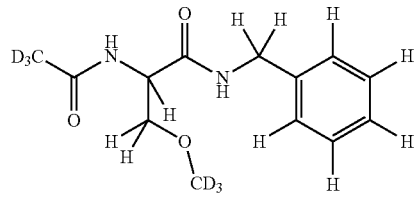 [SMILES: [2H]C([2H])([2H])OCC(NC(=O)C([2H])([2H])[2H])C(=O)NCc1ccccc1]

or a pharmaceutically acceptable salt thereof.

13. The compound of claim 12, wherein the compound is an (R) enantiomer, or a pharmaceutically acceptable salt thereof, which is substantially free of the corresponding (S) enantiomer.

14. The compound of claim 13, wherein any atom not designated as deuterium is present at its natural isotopic abundance.

15. A composition comprising a compound of claim 14 and a pharmaceutically acceptable carrier.

16. The composition of claim 15 for use in treating a disease or disorder associated with aberrant NMDA receptor function.

17. The composition of claim 15 for use in treating epilepsy, diabetic neuropathic pain, fibromyalgia, osteoarthritis, or migraine.

* * * * *

UNITED STATES PATENT AND TRADEMARK OFFICE
CERTIFICATE OF CORRECTION

PATENT NO.        : 8,704,001 B2  
APPLICATION NO.   : 13/119318  
DATED             : April 22, 2014  
INVENTOR(S)       : Craig E. Masse Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 258 days.

Signed and Sealed this

Twenty-ninth Day of September, 2015

Michelle K. Lee  
*Director of the United States Patent and Trademark Office*